(12) United States Patent
Sun et al.

(10) Patent No.: US 10,408,806 B2
(45) Date of Patent: Sep. 10, 2019

(54) ENHANCED NANOSCALE GAS CHROMATOGRAPHY

(71) Applicant: Board of Regents, Ther University of Texas System, Austin, TX (US)

(72) Inventors: Yuze Sun, Grad Prairie, TX (US); Weidong Zhou, Southlake, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 96 days.

(21) Appl. No.: 15/520,611

(22) PCT Filed: Oct. 20, 2015

(86) PCT No.: PCT/US2015/056437
§ 371 (c)(1),
(2) Date: Apr. 20, 2017

(87) PCT Pub. No.: WO2016/064859
PCT Pub. Date: Apr. 28, 2016

(65) Prior Publication Data
US 2017/0315102 A1    Nov. 2, 2017

Related U.S. Application Data

(60) Provisional application No. 62/066,148, filed on Oct. 20, 2014.

(51) Int. Cl.
*G01N 30/74* (2006.01)
*G01N 30/60* (2006.01)
(Continued)

(52) U.S. Cl.
CPC .......... *G01N 30/74* (2013.01); *G01N 30/6095* (2013.01); *G01N 21/3504* (2013.01);
(Continued)

(58) Field of Classification Search
CPC .. G01N 2030/025; G01N 30/26; G01N 30/38; G01N 30/60; G01N 30/6052;
(Continued)

(56) References Cited

U.S. PATENT DOCUMENTS 6,663,697 B1 * 12/2003 Kottenstette ....... G01N 30/6095
73/23.39
7,155,087 B2    12/2006 Suh et al.
(Continued)

OTHER PUBLICATIONS web.archive.org/web/20170709100428/http://www.apixanalytics.com—Archive of www.apixanalytics.com, Jul. 9, 2017.
(Continued)

*Primary Examiner* — Benjamin R Schmitt
(74) *Attorney, Agent, or Firm* — Thomas | Horstemeyer, LLP; David R. Risley; Jason M. Perilla

(57) ABSTRACT

Aspects of enhanced nanoscale gas chromatography are described. In one embodiment, a nano-scale gas chromatography (GC) module includes a light source, a light detector, and a sensor module having vertically-integrated photonic crystal slab (PCS) Fano resonance filter and GC channel layers. The PCS Fano resonance filter layer includes a hole lattice region, and the GC channel layer comprises a gas channel for separation of analytes in a gas mixture. The gas channel includes a coiled section and an extended length section, where the extended length section extends through a region in the GC channel layer that is stacked in proximity with the hole lattice region. The hole lattice region in the PCS Fano resonance filter layer provides local field enhancement of light generated by the light source for increased light-matter interaction with the analytes in the gas channel.

19 Claims, 7 Drawing Sheets

(51) Int. Cl.
*G01N 21/77* (2006.01)
*G01N 21/3504* (2014.01)
*G01N 30/02* (2006.01)

(52) U.S. Cl.
CPC ............... *G01N 2021/7789* (2013.01); *G01N 2030/025* (2013.01)

(58) Field of Classification Search
CPC ....... G01N 2030/6056; G01N 30/6086; G01N 30/6095; G01N 30/62; G01N 30/74; G01N 21/3504; G01N 2021/7789
USPC .............. 73/23.35, 23.4, 23.42, 31.05, 31.06
See application file for complete search history.

(56) References Cited

U.S. PATENT DOCUMENTS

2005/0243321 A1    11/2005    Cohen et al.
2008/0278728 A1*   11/2008    Tetz .................... G01N 21/554
                                                    356/445
2008/0309918 A1    12/2008    Guo et al.

OTHER PUBLICATIONS

International Search Report for PCT/US2015/056437 dated Jan. 19, 2016.
Wright et al., "Chemoselective gas sensors based on plasmonic nanohole arrays." Optical Materials Express, vol. 2, No. 11, Oct. 24, 2012 (Oct. 24, 2012), 8 pages.
Yang et al. "Surface-normal Fano filters based on transferred silicon nanomembranes on glass substrates." Electronis Letters, vol. 44 No. 14, Jul. 3, 2008 (Jul. 3, 2008), 2 pages.
Ameen et al. "Ultra-Sensitive Colorimetric Plasmonic Sensing and Microfluidics for Biofluid Diagnostics Using Nanohole Array." Journal of Nanomaterials, Feb. 18, 2015 (Feb. 18, 2015), 21 pages.

* cited by examiner

ENHANCED NANOSCALE GAS CHROMATOGRAPHY

CROSS-REFERENCE TO RELATED APPLICATIONS

This application is a 35 U.S.C. § 371 national stage application of PCT Application No. PCT/US2015/056437, filed Oct. 20, 2015, and claims the benefit of U.S. Provisional Application No. 62/066,148, filed Oct. 20, 2014, both of which are herein incorporated by reference in their entirety.

STATEMENT REGARDING FEDERALLY SPONSORED RESEARCH

This invention was made with government support under contract 1407947 awarded by the National Science Foundation. The government has certain rights in the invention.

BACKGROUND

Rapid and in-situ chemical vapor analysis provides vital information in many fields, such as environmental monitoring and protection, homeland security and biochemical warfare agent detection, industrial process control and safety monitoring, and healthcare fields, among others. However, most gas sensors lack sensing selectivity, significantly limiting their ability to identify and quantify different volatile organic compounds (VOCs) from real-world samples. In contrast, gas chromatography is a powerful analytical technology and is regarded as a standard method in gas analysis. Gas chromatography relies on the interaction between gas molecules and a polymer coating on gas chromatography columns to separate different molecules and to identify them by their unique retention times. Although current bench-top gas chromatography systems are able to detect hundreds of vapor compounds, they are bulky, power intensive, and usually placed in a centralized lab with dedicated personnel. These bench-top systems are not especially suitable for in-the-field applications.

BRIEF DESCRIPTION OF THE DRAWINGS

For a more complete understanding of the embodiments and the advantages thereof, reference is now made to the following description, in conjunction with the accompanying figures briefly described as follows.

Figure 1:
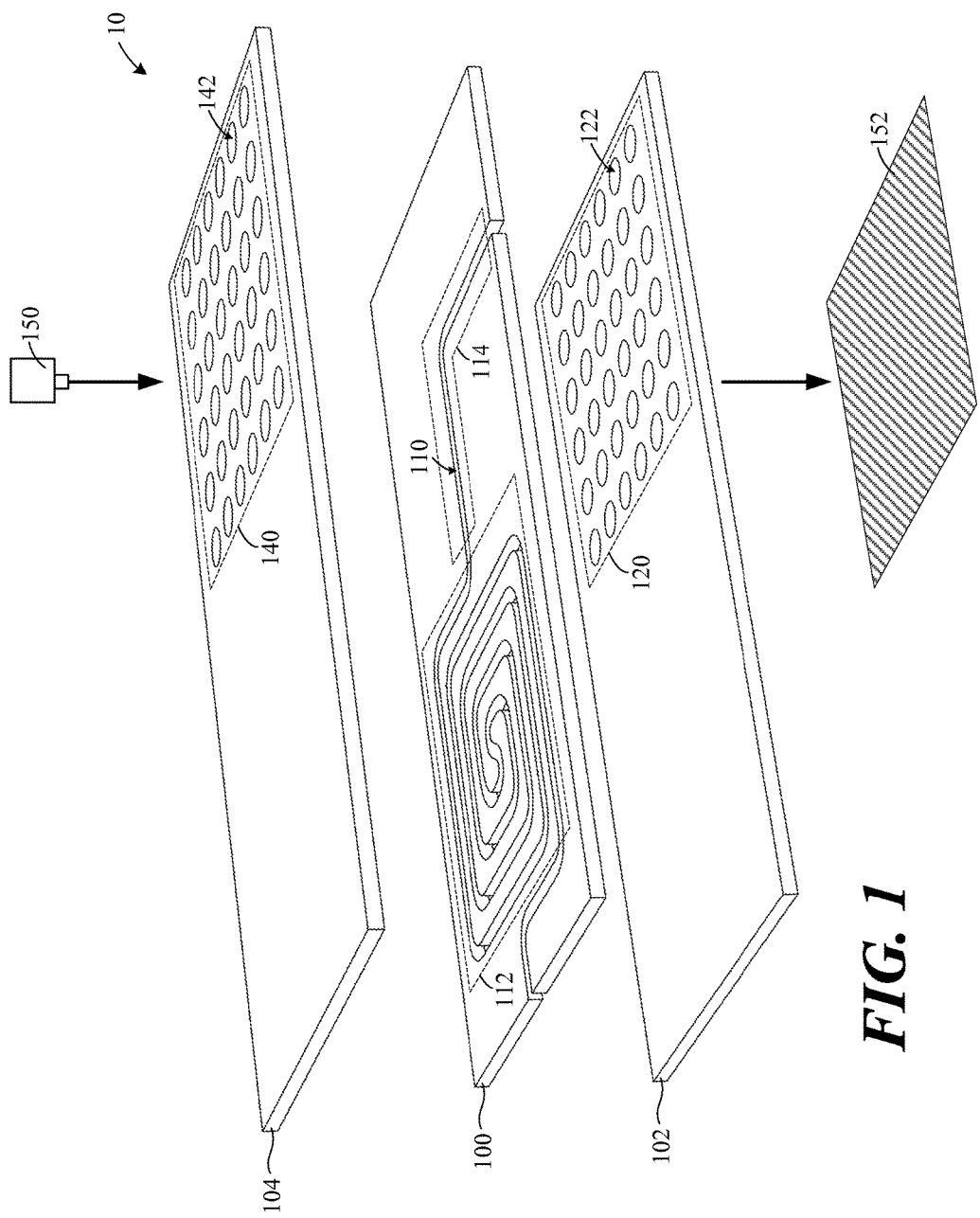
FIG. 1 illustrates an exploded view of an example nano-GC module according to various embodiments described herein.

The drawings illustrate only example embodiments and are therefore not to be considered limiting of the scope of the embodiments described herein, as other embodiments are within the scope of this disclosure. The elements and features shown in the drawings are not necessarily drawn to scale, emphasis instead being placed upon clearly illustrating the principles of the embodiments. Additionally, certain dimensions or positionings may be exaggerated to help visually convey certain principles. In the drawings, similar reference numerals between figures designate like or corresponding, but not necessarily the same, elements.

DETAILED DESCRIPTION

Gas chromatography (GC) systems rely on the interaction between gas molecules and a polymer coating on gas chromatography columns to separate different molecules and identify them by their unique retention times. Although current bench-top gas chromatography systems are able to detect hundreds of vapor compounds, they are bulky, power intensive, and usually placed in a centralized lab with dedicated personnel.

Recently, gas chromatography microsystems (μGC systems) fabricated using micro-electro-mechanical (MEMS) techniques have demonstrated potential for portable, rapid, and low power vapor analyzers. Unfortunately, μGC systems achieve miniaturization and fast analysis at the expense of chromatographic resolution or separation capability. In μGC systems, multiple analytes may co-elute, making it impossible to identify the respective analytes in the co-elution and limiting the complexity of the mixtures that the μGC systems can effectively analyze. To date, different methods have been proposed and explored, including tandem-column μGC systems, comprehensive two-dimensional μGC systems, and pattern responses from micro-sensor arrays. Still, it remains a challenge to achieve fast separation and detection while maintaining adequate chromatographic resolution and a small footprint for effective gas analysis.

It is noted that separation efficiency generally increases with reduced column size in GC systems. In that context, certain performance aspects of bench-top GC, μGC, and nano-GC systems are shown below in Table 1.

TABLE 1

| Performance Aspects of Bench-top GC, μGC, and Nano-GC Systems | | | |
|---|---|---|---|
| | Bench-top GC | μGC | nano-GC |
| Column Dimension | 250 μm | 50 μm | 250 nm |
| Column Length | 30 m | 6 m | 3 cm |
| Separation Time | 100 min | 20 min | 6 sec |

TABLE 1-continued

Performance Aspects of Bench-top
GC, μGC, and Nano-GC Systems

|  | Bench-top GC | μGC | nano-GC |
|---|---|---|---|
| Theoretical Plate Number (N/m) | 4,632 | 23,160 | 4,632,000 |
| Total Plates (N) | 138,960 | 138,960 | 138,960 |

As outlined in Table 1, the typical length of the separation column in a conventional bench-top GC system is about 30 m with a column diameter of about 250 μm. Despite its capability to separate hundreds of chemical vapors, for example, it requires a prolonged analysis time (e.g., ±100 min). By shrinking the size of the separation column down to about 50 μm the μGC system as compared to the bench-top GC system, the length of the separation column can be reduced from about 30 m to about 6 m while maintaining a similar level of separation capability, and the analysis time can be reduced down from about 100 minutes to 20 minutes. However, the performance of μGC systems may not be satisfactory in certain situations where ultra-fast gas analysis is crucial. For example, soldiers in the battlefield and industrial workers may have less than 30 seconds to positively identify and respond to toxic or explosive gases. Similarly, in emergencies, first-responders need timely information about the distribution of various chemical vapors. These unmet challenges highlight the urgent needs for new GC devices in the field of gas analysis.

In an effort to address one or more of the problems outlined above, the embodiments described herein are directed to enhanced nanoscale gas chromatography. In one embodiment, a nano-scale gas chromatography (GC) module includes a light source, a light detector, and a sensor module having vertically-integrated photonic crystal slab (PCS) Fano resonance filter and GC channel layers. The PCS Fano resonance filter layer includes a hole lattice region, and the GC channel layer comprises a gas channel for separation of analytes in a gas mixture. The gas channel includes a coiled section and an extended length section, where the extended length section extends through a region in the GC channel layer that is stacked in proximity with the hole lattice region. The hole lattice region in the PCS Fano resonance filter layer provides local field enhancement of light generated by the light source for increased light-matter interaction with the analytes in the gas channel.

The embodiments described herein provide a number of advantages over known gas analysis devices. For example, the nano-GC modules and systems described herein provide faster gas analysis speed, improved separation capability, improved sensitivity, compact size, and system scalability. The embodiments also mark a step toward wearable, personalized, and ubiquitous sensors accepted and accessible by the general public for various applications, such as indoor air quality monitoring and breathing analysis, for example.

Turning to the drawings, FIG. 1 illustrates an exploded view of an example nano-GC module 10 according to various embodiments described herein. The nano-GC module 10 includes a GC channel layer 100 between two filter layers 102 and 104. The GC channel layer 100 includes a channel 110 formed and extending within it, and the channel 110 includes a coiled section 112 and an extended length section 114. In the nano-GC module 10, the channel 110 serves the purpose of a separation column in a conventional bench-top GC or μGC system. The filter layer 102 includes a hole lattice region 120 embodied as an array of holes 122, and the filter layer 104 includes a hole lattice region 140 embodied as an array of holes 142. Each of the holes 122 extends through the filter layer 102, and each of the holes 142 extends through the filter layer 104.

Figure 2:
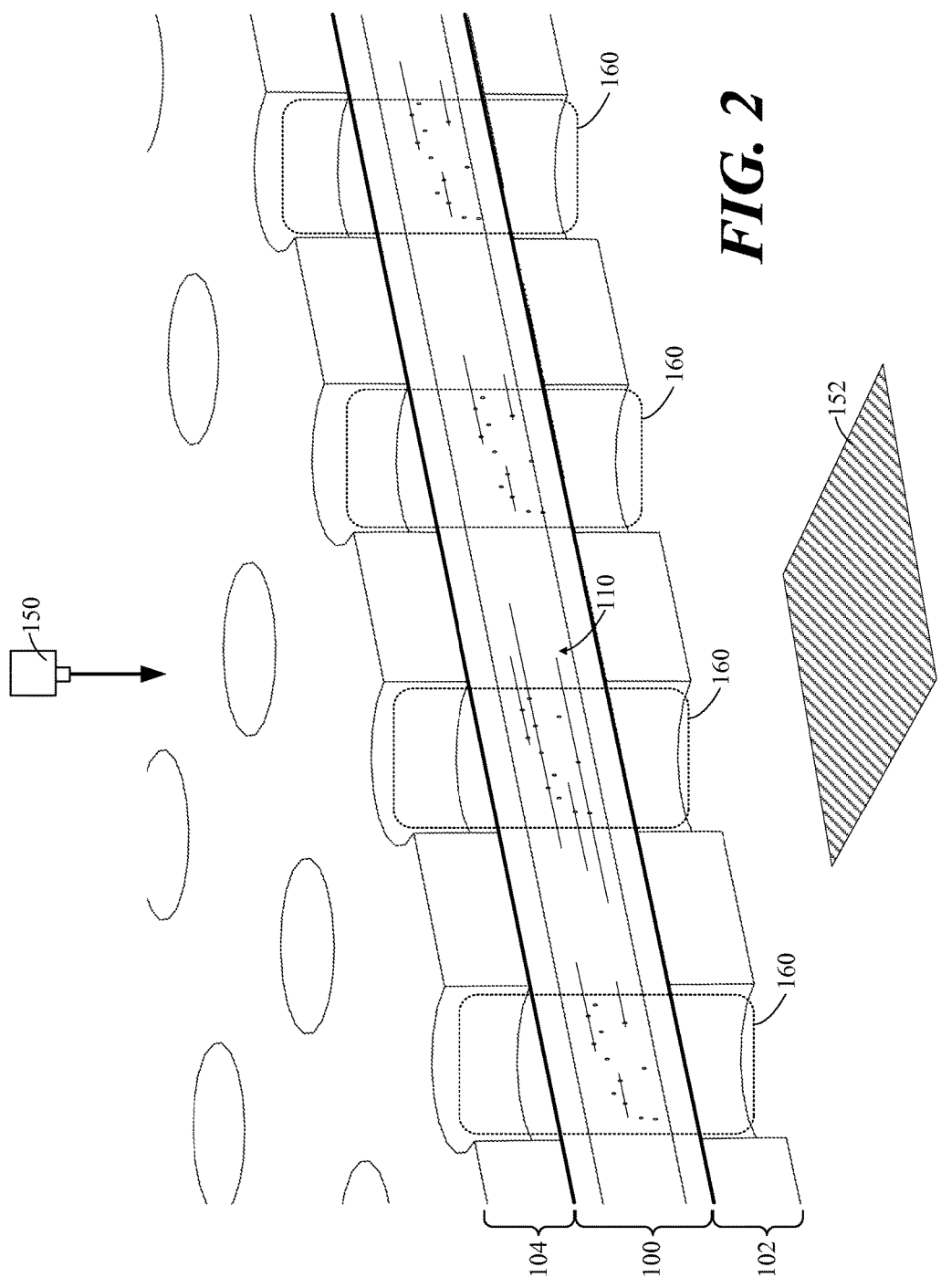
FIG. 2 illustrates a partial cross-sectional view of the example nano-GC module shown in FIG. 1 according to various embodiments described herein.

Before turning to a more detailed description of the structure and function of the nano-GC module 10, it is noted that the illustration in FIG. 1 is provided by way of example. The nano-GC module 10 is drawn in an exploded view in FIG. 1 and not in a final, assembled state. When assembled, the GC channel layer 100 is sandwiched between (e.g., proximate to or in contact with) the filter layers 102 and 104 in a coupled bi-layer PCS vertical stack configuration as shown in FIG. 2. The nano-GC module 10 is also not drawn to scale in FIG. 1. Particularly, the relative and absolute widths, lengths, and depths of the GC channel layer 100 and the filter layers 102 and 104 can vary, together and/or respectively, as compared to that shown. Similarly, the length and cross-sectional dimensions of the channel 110 can vary as compared to that shown.

The shapes and sizes of various structural features in the nano-GC module 10 can also vary from those shown. For example, the length and/or width of the channel 110 can vary from that shown. In that context, the size of the coiled section 112 and, thus, length of the channel 110 can vary among the embodiments. Also, while the coiled section 112 is shown in FIG. 1 as a type of square spiral, the coiled section 112 can be formed in other shapes, such as round, rectangular, and triangular shapes, among others. Further, the size of the hole lattice region 120, the hole lattice region 140, and the individual holes 122 and 142 can vary among the embodiments. Additionally, as described in further detail below, the spacing, pitch, pattern, and/or arrangement of the individual holes and hole latice regions can vary among the embodiments to form hole lattices that differ from those shown in FIG. 1.

While the size of the nano-GC module 10 can vary among the embodiments, the preferred embodiments include one or more physical parameters or features in the nanoscale range. For example, the cross-sectional dimension (e.g., width or diameter) of the channel 110 can range from about 50 to 10,000 nm, although the use of smaller and larger dimensions are within the scope of the embodiments, and the preferred embodiments encompass a cross-sectional dimension (e.g., width or diameter) of the channel 110 from about 50 to 250 nm. The channel 110 can range from about 1 to 100 cm for one or more of the embodiments described herein, although the use of smaller and larger dimensions are within the scope of the embodiments. Similarly, other physical parameters or features of the nano-GC module 10 can be in the nanoscale range, such as the thicknesses of the GC channel layer 100, the filter layers 102 and 104, and/or the diameters of the holes 122 and 142. It should be appreciated, however, that the embodiments are not limited to embodiments or applications in the nanoscale range, as certain physical parameters or features of the embodiments can be scaled up close to (or within) the microscale range.

In one embodiment, the GC channel layer 100 is formed as a layer of dielectric, silica (i.e., $SiO_2$), polycrystalline silicon, or other suitable material(s). As described in further detail below with reference to FIG. 7, the GC channel layer 100 can be directly patterned or deposited onto a glass, quartz, or other substrate of one (or both) of the filter layers 102 and 104. The channel 110 can be formed in the GC channel layer 100 using nanoscale patterning (e.g., electron-beam lithography) and/or dry etching of the silica, for example, among other suitable processing techniques. After being formed, a polymer coating can be applied to the channel 110. For example, a coating of non-polar polydimethylsiloxane (PDMS) and/or polar polyethylene glycol (PEG), among other polymers, can be applied to the channel 110. During operation, the polymer coating of the channel 110 interacts with compounds that flow through the channel 110, leading to different elution times or retention times as would be appreciated in the field of art.

The filter layers 102 and 104 can be embodied as Fano resonance filter layers. In one embodiment, the filter layers 102 and 104 can be embodied as nanomembrane (NM) photonic crystal slab (PCS) Fano resonance filter layers formed in a dielectric, silicon, silica (i.e., $SiO_2$), or other suitable material(s). The NM PCS Fano resonance filters can be formed or transferred onto glass or quartz substrates. As described herein, a Fano resonance filter layer may or may not be inclusive of a glass, quartz, or other substrate. As described in further detail below with reference to FIG. 6, the filter layers 102 and 104 can be formed by patterning silicon NM PCS Fano resonance filters on silicon on insulator (SOI) substrates, for example. Then, the NM PCS Fano resonance filters can be transferred onto glass or quartz substrates using PDMS nanotransfer printing or other suitable processes.

The hole lattice regions 120 and 140 in the filter layers 102 and 104 create the Fano resonance asymmetric lineshape scattering phenomenon when light is applied to the nano-GC module 10. The Fano resonance provides a unique on-column vapor sensing capability with a good detection limit achieved through (1) sharp linewidth as compared to the Lorentzian resonance commonly seen in other photonic structures for high spectral resolution sensing, (2) local field enhancement for significantly increased light-matter interaction, and (3) on-chip integration with nano-GC channels. While the Lorentzian resonance is one fundamental resonance with symmetric lineshape, the Fano resonance exhibits a distinctly asymmetric lineshape and sharp linewidth. Thus, as compared with the Lorentzian resonance, the Fano resonance provides superior spectral resolution when used in optical sensors based on resonance shift measurements.

According to one aspect of the embodiments, when the GC channel layer 100 is sandwiched between the filter layers 102 and 104 in a vertical stack as shown in FIG. 2, the Fano resonance scattering phenomenon concentrates or enhances the field of light near the channel 110. Referring to FIG. 1, the extended length section 114 of the channel 110 extends across or through a region sandwiched between the hole lattice regions 120 and 140. Thus, when light is applied to the hole lattice regions 120 and 140, one or more regions of local field enhancement of the light are created in the extended length section 114 for increased light-matter interaction with analytes in the channel 110. In that way, the nano-GC module 10 can achieve field-enhanced on-column (i.e., on-channel) vapor detection for vapor flowing inside the channel 110. While FIG. 1 shows the extended length section 114 extending between the hole lattice regions 120 and 140 in an "L" shape, the extended length section 114 can extend between the hole lattice regions 120 and 140 in other ways.

As described in further detail below, depending upon certain physical or structural aspects or parameters of the hole lattices 120 and 140 (e.g., hole spacing, hole pitch, lattice pattern, layer thickness, hole pattern alignment, etc.), the Fano resonance scattering phenomenon can be concentrated at certain locations above, below, or in the channel 110, by design. In one embodiment, when the GC channel layer 100 is sandwiched between the filter layers 102 and 104 in a vertical stack as shown in FIGS. 1 and 2, the hole lattice regions 120 and 140 are substantially aligned with each other in the vertical stack. In other embodiments, however, the hole lattice regions 120 and 140 can be offset from each other.

In operation, a vapor or gas mixture is injected (e.g., pumped, pulse pumped, etc.) into the channel 110 of the nano-GC module 10. The vapor travels along the channel 110, which is coated with a relatively thin layer of polymeric stationary phase material. Because different analytes, such as volatile organic compounds (VOCs), interact differently with the polymer coating in the channel 110, they travel along the channel 110 with different elution or retention times and can be identified individually based on their elution or retention times.

To identify the organic chemicals in the channel 110 based on their respective elution or retention times, a light source 150, such as a light-emitting diode, diode laser, tunable diode laser, or other light source or spectrally-tunable light source, can be used to generate light. The light can be focused on the hole lattice region 140 of the nano-GC module 10. In various embodiments, the light can be provided or focused in a direction that is substantially perpendicular to a major surface (e.g., the top) of the filter layer 104 or directed at a suitable angle to the major surface. Based on physical parameters of the hole lattice regions 120 and 140, the light is concentrated or enhanced at a suitable location near or within the channel 110 through the Fano resonance scattering phenomenon. After interacting with the organic chemicals in the channel 110, the light is then detected using a sensor 152, such as an Indium Gallium Arsenide (InGaAs) or other suitable detector. The sensor 152 produces an electrical sense signal that can be analyzed to identify the analytes present in the channel 110.

The structure and operation of the nano-GC module 10 is different than bench-top GC and μGC systems in various aspects. For example, one feature that differentiates the nano-GC module 10 from conventional bench-top GC and μGC systems is the reduced size of the channel 110 as compared to conventional separation columns. With nanoscale reduction of the channel 110, the nano-GC module 10 can achieve capabilities similar to bench-top GC and μGC systems with relatively faster analysis times.

Relatively high separation capabilities have been achieved using tens of meters of larger diameter GC columns (e.g., internal diameter of greater than about 500 μm). However, theoretical and empirical studies show that gas separation efficiency in a GC column increases with decreased column diameter. Additionally, smaller diameter GC columns offer a lower cost solution as a compared to larger diameter GC columns with similar (or better) separation capabilities. Therefore, smaller diameter GC columns (e.g., internal diameter of about 50-250 μm) are commonly used in μGC systems, and nanoscale GC columns or channels are relied upon in the embodiments. The challenge in reducing GC columns down to nanoscale dimensions lie in both the fabrication and integration of nanoscale GC columns or channels GC sensors.

Another feature that differentiates the nano-GC module 10 from conventional bench-top GC and μGC systems is that the nano-GC module 10 relies upon vertical integration. That is, as shown in FIG. 2, the filter layers 102 and 104 are vertically integrated in a vertical stack. The vertical integration of nanoscale GC channels with Fano resonance filter layers, as described herein, permits distributed on-column real-time monitoring of vapor separation processes without interfering with analytes or incurring any dead volumes. According to aspects of the embodiments, ultra-sensitive vapor detection can be achieved from relatively high quality (Q) asymmetric lineshape Fano resonances generated by Fano resonance layers. Particularly, Fano resonance local field enhancement regions that overlap in proximity with nanoscale GC channels significantly increase light-matter interaction within the nanoscale GC channels for greater sensitivity in vapor detection. Among the embodiments, various vertical integration schemes can be relied upon for flexibility as compared to conventional in-plane optical sensing configurations.

Another feature that differentiates the nano-GC modules and systems described herein is that they allow for quick and easy reconfiguration of GC devices for various applications. The nano-GC modules and systems described herein can be easily scaled or interconnected to perform multi-dimensional GC separation (e.g., tandem-column GC, two-dimensional GC, and three-dimensional GC) to further enhance separation capabilities and options. For example, to further increase GC separation resolution, distributed photonic nanosensor arrays can be integrated along a GC channel for real-time monitoring of the separation process of vapor mixtures. Real-time monitoring has been challenging for other types of sensors including those developed for benchtop GC and μGC systems.

FIG. 2 illustrates a cross-sectional view of the vertical stack of the example nano-GC module 10 shown in FIG. 1 taken along the extended length section 114 of the channel 110. As shown, the GC channel layer 100 is arranged between the filter layers 102 and 104 in a vertical stack. In operation, a vapor or gas mixture is injected into the channel 110, and the vapor travels along the channel 110. To identify organic chemicals in the channel 110, light from the light source 150 can be focused on the hole lattice regions 120 and 140 (FIG. 1) of the vertical stack. Due to the structure of the hole lattice regions 120 and 140 and their arrangement in the vertical stack, the light is enhanced by the Fano resonance scattering phenomenon across the channel 110. As shown in FIG. 2, the light is enhanced in the regions 160 between the filter layers 102 and 104 and through the channel 110. As discussed above with reference to FIG. 1, after interacting with analytes in the channel 110, the light is then detected using the sensor 152.

With reference to the example provided in FIG. 2, it is noted that the nano-GC devices described include one or more gas channels sandwiched between or coupled against one or more Fano resonance filter layers. In the embodiments, analyte detection can be implemented anywhere along the gas channel. Such flexibility in detection location provides better chromatographic resolution to resolve gas peaks that may not be resolvable otherwise. Furthermore, the field enhancement of light using the Fano resonance filter layers can be tuned or localized to concentrate on the gas channel for enhanced detection sensitivity as described in greater detail below.

Figure 3A:
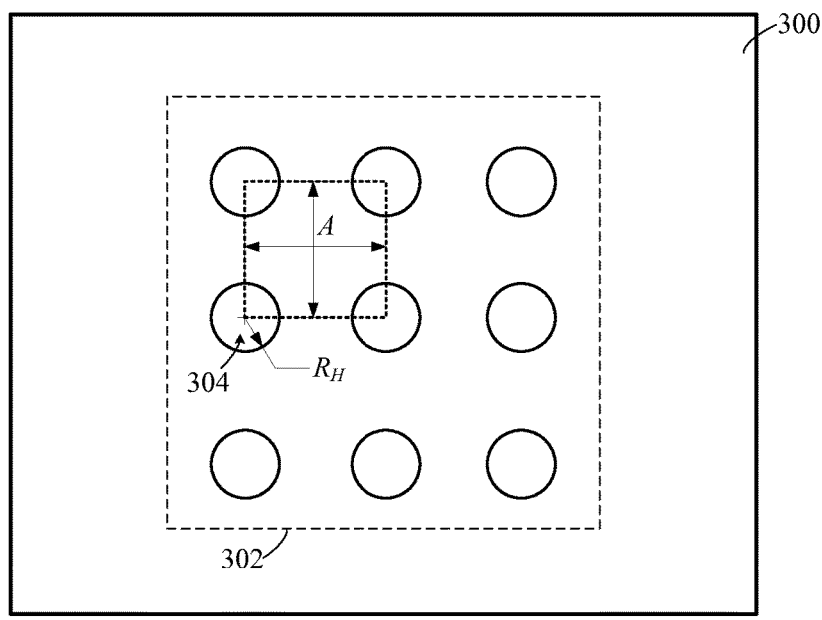
FIG. 3A illustrates physical design parameters of a Fano resonance filter layer for localization of field enhancement according to aspects of the embodiments described herein.
Figure 3A:
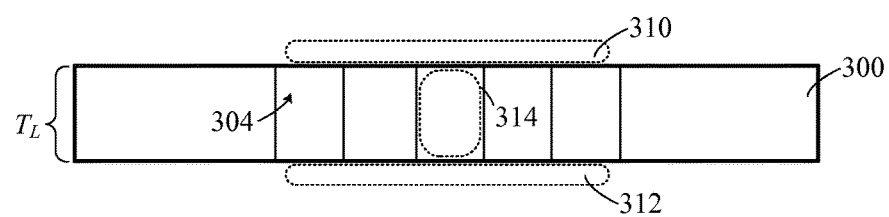

In the context of the structures shown below in FIGS. 3A-3D, it is clear that optical sensors can be formed as bi-layers, variations of hybrid bi-layers, or single layer PCS structures. FIG. 3A illustrates physical design parameters of a Fano resonance filter layer 300 for localization of field enhancement according to aspects of the embodiments described herein. In FIG. 3A, both top-down and side views of the filter layer 300 are shown. The filter layer 300 includes a hole lattice region 302 including holes 304 arranged in a square periodic array. Each of the holes 304 has a radius $R_H$, and an area A exists between four of the holes 304 in the hole lattice region 302. Further, the filter layer 300 has a thickness $T_L$. These physical design parameters of the filter layer 300, along with other structural and/or environmental parameters, such as the material(s) from which the filter layer 300 is formed, the ambient temperature, etc. present factors for localization of field enhancement.

Figure 3B:
FIG. 3B illustrates physical design parameters of a vertical stack including a Fano resonance filter layer for localization of field enhancement according to aspects of the embodiments described herein.

FIG. 3B illustrates physical design parameters of a vertical stack including the Fano resonance filter layer 300 coupled with an unpatterned layer 320 with an air gap existing between the layers. Although the Fano resonance filter layer 300 is shown above the unpatterned layer 320 in FIG. 3B, the Fano resonance filter layer 300 can be formed below the unpatterned layer 320. In other words, in variations of the integration scheme shown in FIG. 3B, a GC channel layer can be placed on top or bottom of a bi-layer PCS structure, addition to be placed in the middle. Also, a nano-GC channel layer can be formed between the filter layer 300 and the unpatterned layer 320. The unpatterned layer 320 can be formed from the same or different materials as the filter layer 300, but omits the holes 304. The vertical stack shown in FIG. 3B provides a coupled cavity configuration for localization of field enhancement. Among others, the physical design parameters for localization of field enhancement in FIG. 3B include the material(s) used for the unpatterned layer 320, the thickness of the unpatterned layer 320, and the size of the air gap (if any).

A high Q optical filter is feasible with the configuration shown in FIG. 3B, although the asymmetric field concentration associated with the asymmetric cavity configuration may reduce the overlap between the optical field and the nano-channel between the two coupled layers. This may limit the cavity enhancement in gas sensing. However, this configuration offers fabrication flexibility, as there is no lattice displacement impact and there is no requirement for lattice alignment between two coupled layers.

Figure 3C:
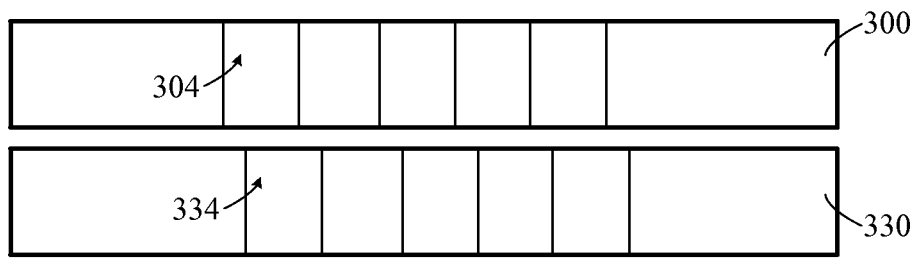
FIG. 3C illustrates physical design parameters of a vertical stack including two Fano resonance filter layers with offset hole lattices for localization of field enhancement according to aspects of the embodiments described herein.

FIG. 3C illustrates physical design parameters of a vertical stack including the Fano resonance filter layer 300 coupled with a Fano resonance filter layer 330 having offset hole lattices for localization of field enhancement. As shown in FIG. 3C, the filter layer 300 includes the holes 304, and the filter layer 330 includes the holes 334. In the stack of the filter layer 300 coupled with the filter layer 330, the holes 304 are offset from the holes 334. This configuration is different than that discussed above with reference to FIGS. 1 and 2, where the holes 122 were substantially aligned with the holes 142. Among others, the physical design parameters for localization of field enhancement in FIG. 3C include the offset distance between the holes 304 and 334, and the size of any gap between the filter layers 300 and 330. It is noted the offset in the holes of the Fano resonance filters shown in FIG. 3C can be applied to other embodiments described herein, such as that shown in FIG. 1.

Figure 3D:
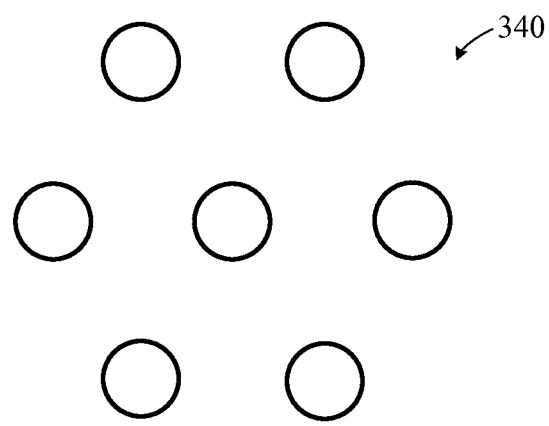
FIG. 3D illustrates an example honeycomb periodic array of a Fano resonance filter layer according to aspects of the embodiments described herein.

FIG. 3D illustrates an example honeycomb periodic array 340 of a Fano resonance filter layer according to aspects of the embodiments described herein. Here, it is noted that the use of lattices or arrays other than the square arrays shown in FIGS. 1, 2, and 3A are within the scope of the embodiments. The honeycomb periodic array 340 shown in FIG. 3D can be used to achieve other Q factors and/or symmetric or asymmetric lineshapes and alternative linewidths, for example. Other embodiments can rely upon other periodic and/or aperiodic hole arrangements, such as radial and graduated arrangement, among others.

Thus, according to aspects of the embodiments, one or more filter layers can be designed to create relatively stronger constructive interference or field enhancement at certain locations. For example, in some embodiments, one or more filter layers can be designed for field enhancement in a region where a polymer coats a GC channel and not at other locations within the GC channel. This type of localized field enhancement enhances the detection sensitivity and lowers noise, thus achieving better sensing signal-to-noise ratios.

Due to the Fano resonance effect, the transmission and the reflection spectra of the filter layers described herein (and vertically integrated combinations thereof) have high Q factors with close to zero linewidths and sharp transitions between transmission peaks and dips. With the choice of the proper design parameters, the Q factor and the symmetry of the resonance can be tuned to have either symmetric or asymmetric lineshape and controlled field concentration modal profiles.

Figure 4:
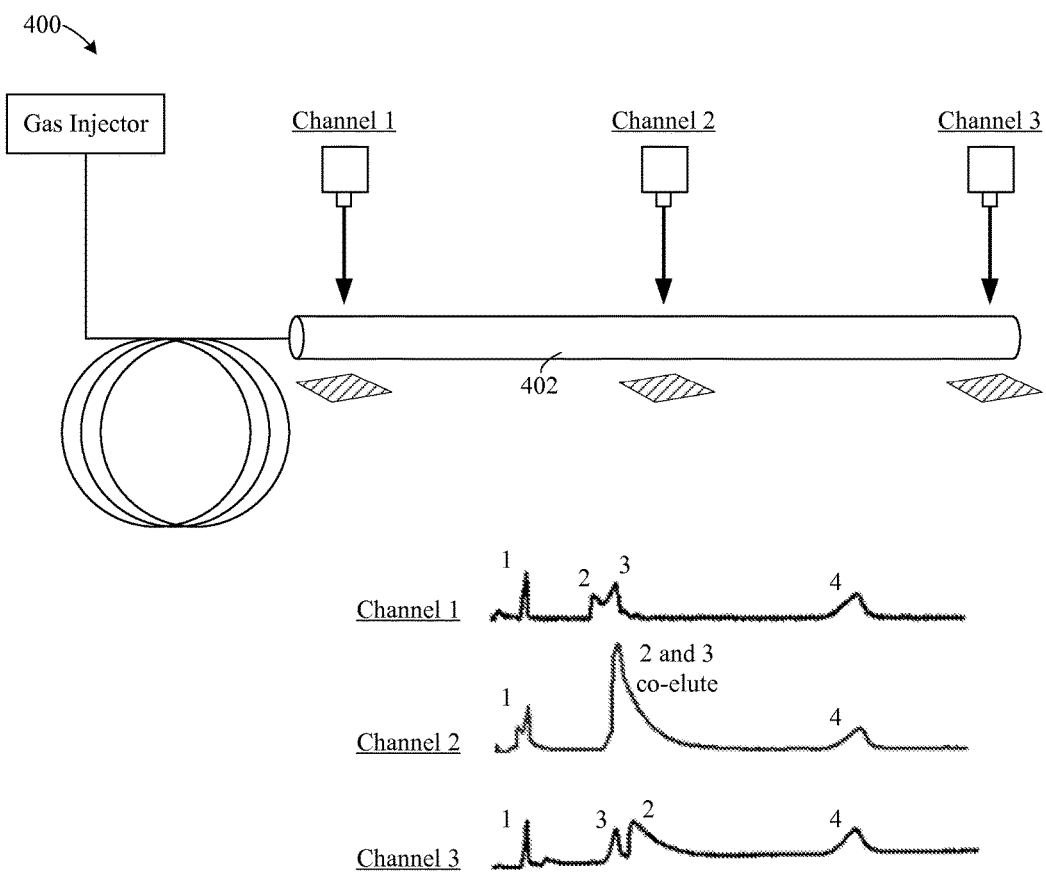
FIG. 4 illustrates a tandem-column GC system with three on-column detectors for a discussion of the benefits of distributed on-column detection according to aspects of the embodiments described herein.

Before turning to FIG. 4, it is noted that nearly all detection in conventional GC devices is carried out at the end of a GC column, a technique which is called terminal detection. Terminal detection schemes can introduce certain problems. First, when detection in a GC device is carried out at the end of a GC column, the end-column detector may not be compatible with the GC fluidics, resulting in dead volumes. Further, elution peaks may be skewed or broadened due to such incompatibility. The introduction of an end-column detector may also interfere with the flow inside a GC column, affecting the vapor separation. Also, some end-column detectors are destructive. For example, the flame ionization detector (FID) relies on burning samples to generate a sensing signal. Those drawbacks are exacerbated for multi-dimensional GC devices where multiple columns are cascaded and samples need to be transported efficiently from an upstream column to a downstream one while still preserving the separation acquired in the upstream column. Further, since an end-column detector obtains information only after chemical vapors have undergone separation, no information (or even misleading information) can be provided about the separation processes along the column.

As compared to terminal detectors, an on-column detector detects chemical vapors flowing inside a GC column or channel without interference with the gas flow. On-column detectors are non-destructive and do not introduce dead volume. Thus, on-column detectors are particularly useful for the development of multi-dimensional GC devices (i.e., tandem-column GC, two-dimensional GC, and three-dimensional GC devices) where multiple columns are connected and the elution from each column can be monitored separately. Additionally, deploying multiple on-column detectors along a single GC column or channel provides other benefits. For example, using multiple on-column detectors enables real-time monitoring of vapor separation processes, significantly improving chromatographic resolution.

FIG. 4 illustrates a tandem-column GC system 400 with three on-column detectors for a discussion of the benefits of distributed on-column detection according to aspects of the embodiments described herein. In the GC system 400, three detection channels 1-3 are presented at three respective locations along a GC column 402. Using the GC system 400, the separation of analytes 1-4 can be monitored in real-time. By comparing the chromatogram measured on the three detection channels 1-3, it can be seen in FIG. 4 that analytes 2 and 3, which were well separated at the location of channel 1, co-eluted at the location of channel 2, but were separated again at the location of channel 3 (with the elution sequence switched). Without the combined on-column detection capability and distributed sensor array format provided by the GC system 200, such information would have been lost. For example, if an end-column sensor was used, the information would have been lost.

The concepts presented in FIG. 4 demonstrate that obtaining independent and complementary information from a distributed on-column sensor array significantly improves GC separation capability. However, the lack of suitable sensor-column integration techniques in the field makes it challenging to implement on-column detection concepts. Further, the lack of good sensor-column integration techniques limits the number of on-column sensors that can be deployed along a GC column or channel. Especially when moving to nano-GC devices with smaller channel sizes, the challenges are more difficult. The embodiments described herein provide a unique solution that enables robust and seamless integration between one or more nano-GC channels and on-column detectors. According to aspects of the embodiments described below, multiple on-column or on-channel detection regions can be deployed along one or more nano-GC channels.

Figure 5:
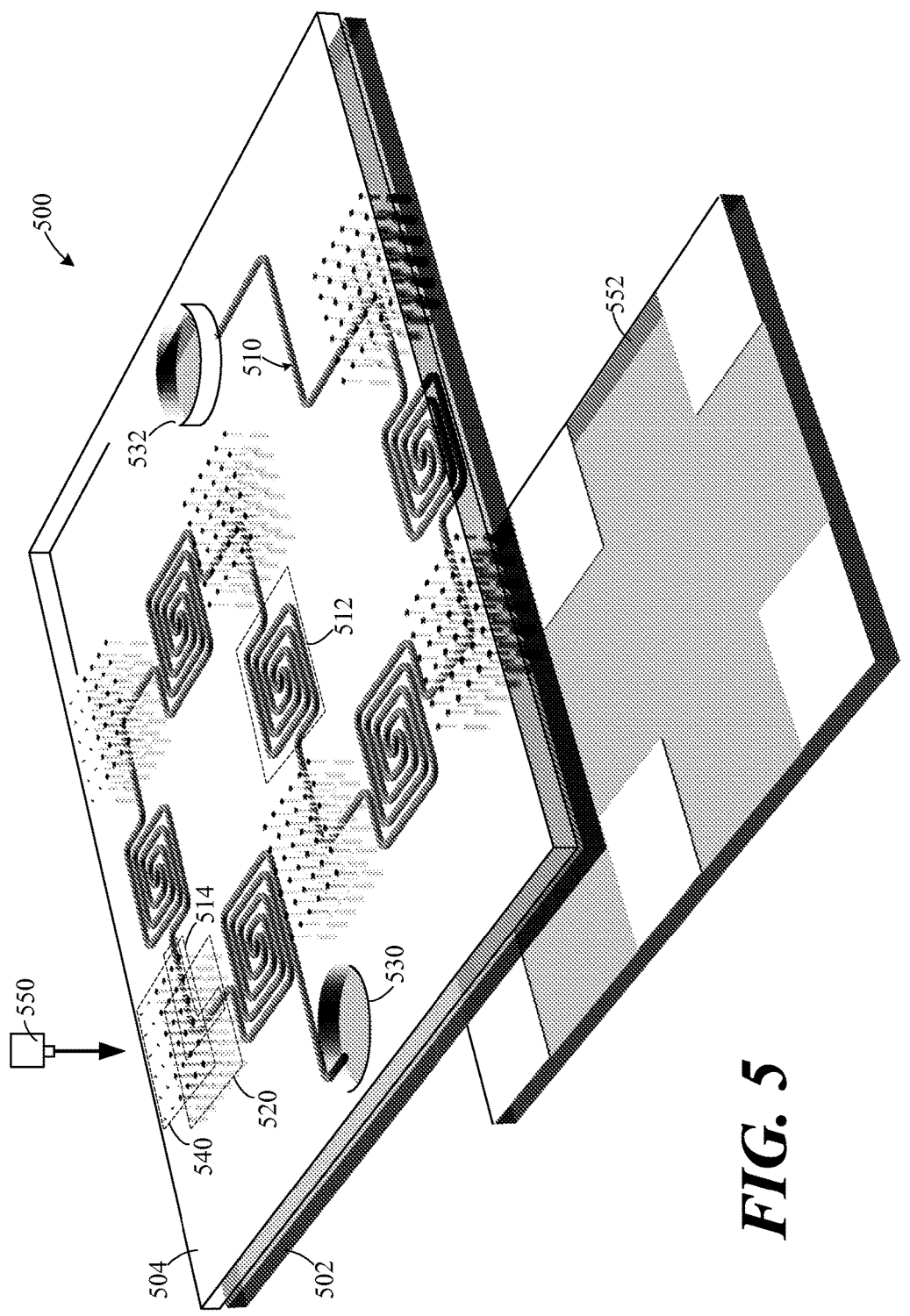
FIG. 5 illustrates an example nano-GC distributed on-column sensor module array according to various embodiments described herein.

FIG. 5 illustrates an example nano-GC distributed on-column sensor module array 500 according to various embodiments described herein. The nano-GC module array 500 includes a GC channel layer between two filter layers 502 and 504. The GC channel layer includes a channel 510 extending within it, and the channel 510 includes a number of coiled sections 512 and a number of extended length sections 514. In the nano-GC module array 500, the channel 510 serves the purpose of a separation column in a conventional bench-top GC or μGC system. Consistent with the embodiments described above, the filter layer 502 includes a number of hole lattice regions 520 embodied as an array of holes, and the filter layer 504 includes a hole lattice region 540 embodied as an array of holes.

It is noted that the illustration in FIG. 5 is provided by way of example. The nano-GC module array 500 is not drawn to scale in FIG. 5. Particularly, the relative and absolute widths, lengths, and depths of the GC channel layer and the filter layers 502 and 504 can vary, together and/or respectively, as compared to that shown. The sizes of various structural features in the nano-GC module array 500 can also vary from those shown. For example, the length and/or diameter of the channel 510 can vary from that shown. In that context, the size of the coiled sections 512 and, thus, length of the channel 510 can vary among the embodiments. Similarly, the size and positions of the hole lattice regions 520 and 540 can vary among the embodiments.

While the size of the nano-GC module array 500 can vary among the embodiments, the preferred embodiments include one or more physical parameters or features in the nanoscale range. For example, the cross-sectional dimension of the channel 510 can range from about 50 to 10,000 nm, although the use of smaller and larger dimensions are within the scope of the embodiments, and the preferred embodiments encompass a cross-sectional dimension of the channel 510 from about 100 to 250 nm. The channel 510 can range from about 1 to 100 cm for one or more of the embodiments described herein, although the use of smaller and larger dimensions are within the scope of the embodiments. Similarly, other physical parameters or features of the nano-GC module array 500 can be in the nanoscale range.

In one embodiment, the GC channel layer in the nano-GC module array 500 is similar to the GC channel layer 100 in FIG. 1, but the channel 510 is longer than the channel 110. In that context, the GC channel layer in the nano-GC module array 500 can be directly patterned or deposited onto a glass, quartz, or other substrate of one (or both) of the filter layers 502 and 504. The channel 510 can be formed in the GC channel layer using nanoscale patterning (e.g., electron-beam lithography) and/or dry etching of silica, for example, among other suitable processing techniques. After being formed, a polymer coating can be applied to the channel 510.

As described above, the polymer coating of the channel 510 interacts with compounds that flow through the channel 510, leading to different elution times or retention times as would be appreciated in the field of art.

The filter layers 502 and 504 can be embodied as Fano resonance filter layers. In one embodiment, the filter layers 502 and 504 can be embodied as NM PCS Fano resonance filter layers formed in a dielectric, silicon, silica, or other suitable material(s). As described in further detail below with reference to FIG. 6, the filter layers 102 and 104 can be formed by patterning silicon NM PCS Fano resonance filters on silicon on insulator (SOI) substrates, for example. Then, the NM PCS Fano resonance filters can be transferred onto glass or quartz substrates using polydimethylsiloxane (PDMS) nanotransfer printing or other suitable processes. Thus, the filter layers 502 and 504 can include NM PCS Fano resonance filters on glass, quartz, or other suitable optical substrates.

The hole lattice regions 520 and 540 in the filter layers 502 and 504 create the Fano resonance asymmetric lineshape scattering phenomenon when light is applied to the nano-GC module array 500. As shown in FIG. 5, when the GC channel layer is sandwiched between the filter layers 502 and 504 in a vertical stack, the Fano resonance scattering phenomenon concentrates or enhances the field of light near the channel 510. Referring to FIG. 5, it can be seen that one extended length section 514 of the channel 510 extends across or through a region sandwiched between the hole lattice regions 520 and 540. This area comprises one of six detection regions in the nano-GC module array 500. When light is applied to the hole lattice regions 520 and 540 by the light source 550, one or more regions of local field enhancement of the light are created in the extended length section 514 for increased light-matter interaction with analytes in the channel 510. In that way, the nano-GC module array 500 can achieve field-enhanced on-column (i.e., on-channel) vapor detection for vapor flowing inside the channel 510. Because the nano-GC module array 500 includes six detection regions, it provides distributed on-column detection capabilities at different locations over the length of the channel 510.

In operation, a vapor or gas mixture is injected (e.g., pumped, pulse pumped, etc.) into one of the inlet ports 530 and 532 in the filter layer 504 and, thus, the channel 510. The vapor travels along the channel 510, which is coated with a relatively thin layer of polymeric stationary phase material. Because different analytes interact differently with the polymer coating in the channel 510, they travel along the channel 110 with different elution or retention times and can be identified individually based on their elution or retention times. To identify the analytes in the channel 510, a light source 550 can be used to focus light on the hole lattice regions 540 and 520. Similarly, the light source 550 or other light sources can be used to focus light at the other detection regions of the nano-GC module array 500. In various embodiments, the light sources can provide the same or different wavelengths of light at respective detection regions. Based on physical parameters of the hole lattice regions 520 and 540, the light is concentrated or enhanced at a suitable location near or within the channel 510 through the Fano resonance scattering phenomenon. After interacting with the analytes in the channel 510, the light is then detected using a sensor array 552. The sensor array 152 produces an electrical sense signal that can be analyzed to identify the analytes present in the channel 510. The sensor array 152 can include a sensor for each of the detection regions of the nano-GC module array 500. In other embodiments, multiple nano-GC module arrays similar to the nano-GC module array 500 can be chained together in fluid communication with each other in a tandem-column, two-dimensional, and/or three-dimensional GC system for additional flexibility and analysis.

Figure 6:
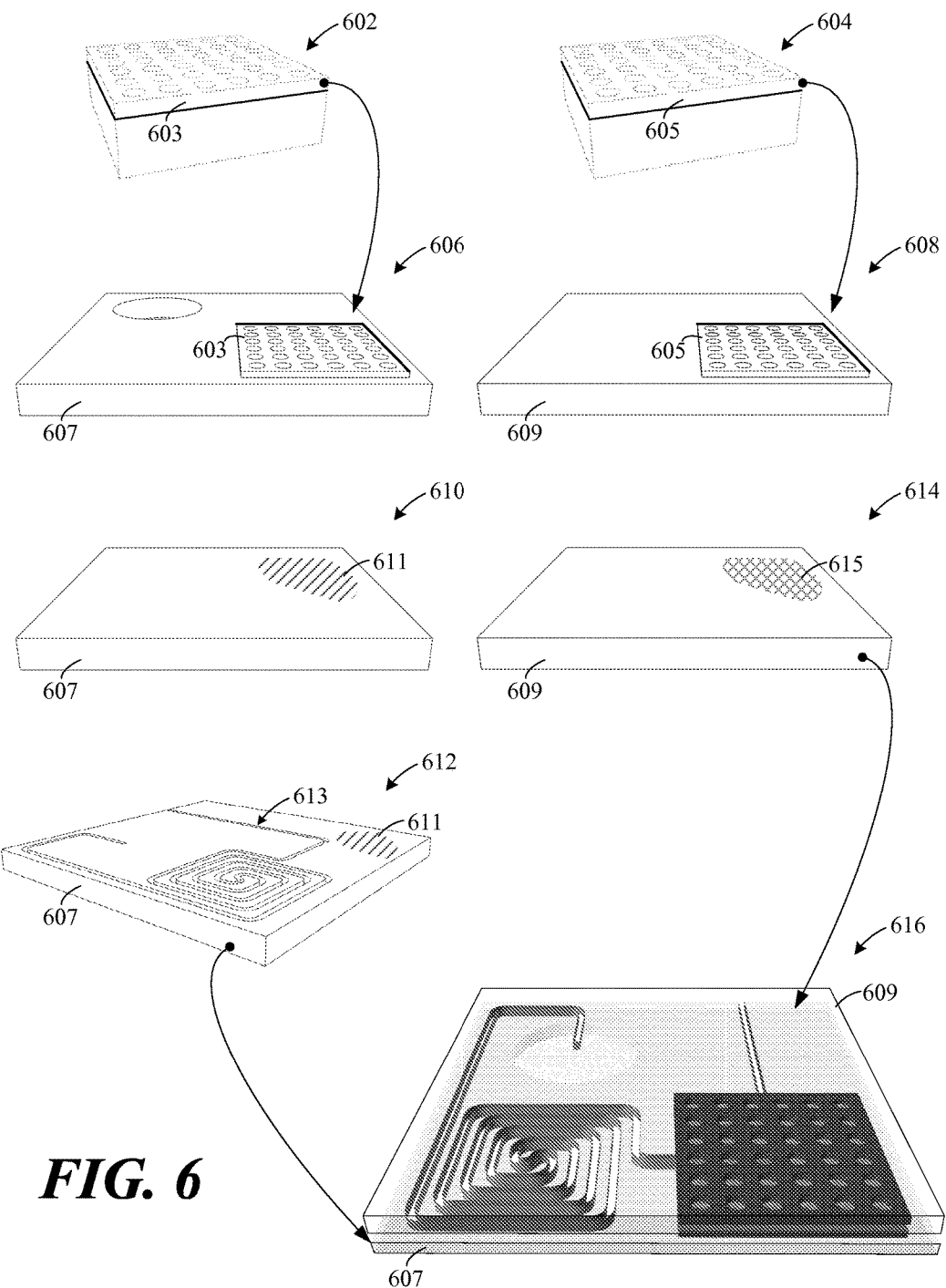
FIG. 6 illustrates an example process for forming a gas chromatography module according to various embodiments described herein.

FIG. 6 illustrates an example process for forming a gas chromatography module according to various embodiments described herein. At reference numerals 602 and 604, the process includes forming first and second Fano resonance filter layers 603 and 605 on dielectric, silicon, silica, or other suitable material(s). At reference numeral 606, the process includes transfer printing the first Fano resonance filter 603 onto a first glass, quartz, or other optical substrate 607. As shown, the optical substrate 607 can include one or more pre-drilled inlet or outlet ports.

At reference numeral 606, the process includes transfer printing the second Fano resonance filter 605 onto a second glass, quartz, or other optical substrate 609. Although not shown, the optical substrate 609 can also include one or more pre-drilled inlet or outlet ports. In one embodiment, micro-contact printing can be relied upon at reference numerals 602, 604, 606, and/or 608. Micro-contact involves lithography that uses relief patterns on a master PDMS stamp to form patterns on a surface of a substrate through conformal contact.

At reference numeral 610, the process includes directly patterning or depositing (e.g., via chemical vapor deposition) a layer of dielectric, silica, polycrystalline silicon, or other suitable material(s) 611 onto the substrate 607 and over the first Fano resonance filter 603. At reference numeral 610, the process can further include chemical and/or mechanical polishing of the material 611, for surface planarization.

At reference numeral 612, the process includes forming at least one nano-GC channel 613 in the material 611 using nanoscale patterning (e.g., electron-beam lithography) and/or dry etching. At reference numeral 612, the process can further include coating the nano-GC channel 613 with a polymer. For example, the nano-GC channel 613 can be coated with one or both of non-polar PDMS and/or polar PEG. Those polymers can be dissolved in organic solvent such as acetone and then diluted based on the desired coating thickness.

The quality of the stationary phase coating is an important factor in the performance of the nano-GC column 613. A 10-20 nm layer, for example, of polymer on the inner surface of nano-GC column 613 can be applied. Both non-polar PDMS and highly polar PEG can be used among other polymers. Those polymers can be dissolved in organic solvent such as acetone first and then diluted based on the desired coating thickness. A syringe or other pump can be used to push a polymer solution through the nano-GC channel 613. After the nano-GC channel 613 is filled with the polymer solution, it can be left incubated for a period of time. Then, a vacuum can be applied to one end of the nano-GC channel 613 for a period of time to evaporate the solvent while the other end is sealed. After vacuum, the nano-GC column 613 can be baked in an oven at 50-70° C., for example, to cross-link the coating and strengthen its mechanical properties.

At reference numeral 614, the process includes applying a spin on glass (SOG) or other suitable coating 615 on the second substrate 609 and over the second Fano resonance filter 605. At reference numeral 610, the process can further include patterning or depositing a layer of dielectric, silica, polycrystalline silicon, or other suitable material(s) over the SOG coating 615.

At reference numeral 616, the process includes aligning and bonding the layers together in a vertical stack to encapsulate the nano-GC channel 613 and finalize the coupled optical sensors. The alignment can be accomplished with a wafer bonding aligner or other suitable tools. Although the process in FIG. 6 is shown for forming one detection region, any number of detection regions can be formed using this process.

In addition to gas separation, the embodiments described herein can be relied upon to develop nanoscale optofluidic vapor sensors or sensor arrays, where a concentration of single gas of particular interest can be quantitatively measured and monitored in real-time. Similar to the tri-layer vertical structure used in FIGS. 1 and 5, a gas fluidics chamber can be designed and fabricated between one or more Fano resonance filters. However, rather than a channel between one or more Fano resonance filters as in FIGS. 1 and 5, the nanoscale optofluidic vapor sensor embodiments include a larger gas fluidics chamber fabricated between one or more Fano resonance filters. The Fano resonance filters can be separated by a suspension layer (i.e., air gap) of several tens to several hundreds of nanometers to fabricate the gas fluidics chamber. In some cases, a gas fluidics chamber is an intrinsic part of a coupled NC PCS Fano resonance filter. Therefore, an efficient nanoscale gas fluidic chamber can be achieved with simplicity and no additional dead volume, resulting in fast sensor response.

Gas detection in the nanoscale optofluidic vapor sensor embodiments can be achieved through coating a thin layer of polymer on the surface of the PCS Fano resonance filters in the gas fluidics chamber. Depending upon the number of detection regions in the optofluidic vapor sensor, any number of different polymers can be used at respective detection regions. For example, for a nanoscale optofluidic vapor sensor array similar to the nano-GC module array 500 shown in FIG. 5, six different polymers can be used at the six different detection regions to functionalize the sensor surface. In that way, a pattern response to the same vapors can be generated simultaneously and used for pattern recognition and profiling vapor mixtures with enhanced specificity. In one case, the gas fluidics chamber can be fabricated between a Fano resonance filter coupled with another layer of material (e.g., as in FIG. 3B). In another case, the gas fluidics chamber can be fabricated between two Fano resonance filters as described herein.

The embodiments described herein can be used to investigate the relationship between pressure and gas flow rate for various channel sizes and lengths for both helium and dry air, both of which can be used as a nano-GC carrier gas for different applications. In that context, micro/nanoscale gas flow is characterized by Knudsen number, $Kn=\lambda/L$, where $\lambda$ is the mean free path of gas molecules and $L$ is the characteristic length scale of the flow (or device). A classification of different flow regimes is given as: $Kn<0.001$, continuum flow regime; $0.001<Kn<0.1$, slip flow regime; $0.1<Kn<10$, transition flow regime; and $10<Kn$, free molecular flow regime. For air molecules at 1 atm and 25° C., the mean path length is approximately 70 nm. Thus, the operation of nano-GC devices lies in the transition flow regime.

Helium is inert and has the lowest density and viscosity among all the GC carrier gases. Thus, Helium can be used as a model to study the fluidic flow and gas separation in nanoscale devices. At the same time, the use of dry air as the carrier gas is desirable in portable GC systems because it is readily available from the ambient environment and reduces the complexity of GC systems. However, since dry air has higher viscosity, the nano-GC performance is expected to deteriorate as compared with helium.

The Golay equation can be employed to calculate the total plate height H:

$$H = B \cdot u + C_s \cdot u + C_m \cdot u \quad (1),$$

where B is a constant that accounts for the of a vapor analyte, Cs and Cm describe the mass transfer and account for the finite time required to reach equilibrium in the stationary phase and the mobile phase, u is the linear velocity of the carrier gas flow. H is one important parameter to characterize GC separation efficiency, as it is inversely proportional to the total plate number, N, via $N \propto 1/H$. H is highly dependent upon GC channel size, polymer coating properties (polar and non-polar) and thickness, analyte diffusion rate in the stationary and mobile phases, as well as the carrier gas flow rate. Equation (1) shows that there is a singular velocity where the plate height exhibits a minimum value and, thus, the best separation efficiency.

The H value for various channel sizes (e.g., 100-1000 nm) and polymer thicknesses (e.g., 1-50 nm) can be evaluated to settle on suitable design parameters. Further, two types of polymers, PDMS and PEG, can be used as model polymers in nano-GC channels. For evaluation, any of the analytes shown in Table 2 (or others) can be chosen, among which 31 are related to hazardous workplace chemicals by the California Standard Section 01350 Specification.

The 50 analytes in Table 2 have wide range of vapor pressures, polarities, and diffusion rates. The optimal H can be simulated for each analyte. Finally, temperature, which the Golay equation, can be varied from room temperature to 50° C. and the corresponding H can be calculated accordingly.

TABLE 2

List of 50 VOCs

| Formaldehyde* | Acetaldehyde* | Isopropanol* | Ethanol | Cyclohexane |
|---|---|---|---|---|
| Isophorone* | Dioxane* | Vinyl acetate* | Dichloroethylene* | Trichloroethylene* |
| Hexaldehyde | 2-Heptanone | n-Hexane* | 2,4-Dimethylpentane | n-Heptane |
| n-Octane | n-Nonane | n-Decane | n-Undecane | n-Dodecane |
| Toluene* | Ethylbenzene* | m-Xylene* | Styrene* | Benzene* |
| Carbon tetrachloride* | Limonene | Halogens | Chloroform* | 1,2-Dichloroethane |
| Phenol* | Dimethylformamide* | Ethylene glycol* | Methyl chloroform* | Carbon disulfide* |
| Tetrachloroethylene* | p-Dichlorobenzene* | Ethyl acetate | Butyl acetate | Acetone |
| Methyl t-butyl ether* | Methylene chloride* | Chlorobenzene* | Cyclohexane | Trimethylbenzene |
| Ethylene glycol | Ethylene glycol | Ethylene | Ethylene glycol | Propylene |

TABLE 2-continued

List of 50 VOCs

| Formaldehyde* | Acetaldehyde* | Isopropanol* | Ethanol | Cyclohexane |
|---|---|---|---|---|
| monoethyl ether acetate* | monomethyl ether* | glycol monomethyl ether acetate* | monoethyl ether* | glycol monomethyl ether* |

*Denotes a workplace hazardous VOC.

The interaction of analytes with polymer coatings on nano-GC channels can be characterized by their respective partition constant K, which determines their retention time in the nano-GC channels. For each analyte, K can be calculated by $$K = \exp\left(-\frac{\Delta G}{RT}\right),$$

where ΔG is the Gibbs free energy change when gas molecules are adsorbed onto the polymer coating, R is the general gas constant, and T is the absolute temperature. Various nano-GC parameters, such as channel size/length and polymer coating polarity/thickness, and separation conditions, such as flow rate and temperature, can be evaluated as design parameters. Additionally, different configurations of GC channels, such as one dimensional nano-GC and tandem nano-GC channels, where two nano-GC channels are coated with different polymers, can be compared. The elution broadening effect can also be added to each analyte peak, which can be estimated by the Golay equation. Through simulations, for example, the total separation time and total number of peaks that can be adequately separated can be estimated as design parameters in various embodiments.

The reduction of the PCS Fano resonance layer size is favorable for the compact design of the nano-GC modules described herein. Among other parameters, the optical Q factor depends on the number of the lattice period in the filter layers, particularly when the lattice period is less than 20. Thus, other lateral confinement configurations, such as lateral PCS heterostructure design concepts, can be used to reduce the cavity size while offering high Q filter design with reduced lateral dimensions.

The terms "a" and "an" are to be interpreted as one or more unless explicitly stated otherwise. The term "substantially" is defined as largely but not necessarily wholly what is specified (and includes what is specified, e.g., substantially 90 degrees includes 90 degrees and substantially parallel includes parallel). In any disclosed embodiment, the terms "substantially," "approximately," and "about" may be substituted with "within [a percentage] of" what is specified, where the percentage includes 0.1, 1, 5, and 10 percent.

Various terms used herein, such as "comprise" (and any form of comprise, such as "comprises" and "comprising"), "have" (and any form of have, such as "has" and "having"), "include" (and any form of include, such as "includes" and "including"), "contain" (and any form of contain, such as "contains" and "containing"), "based," "according to," and "in response to," among others, are open-ended unless explicitly stated otherwise. For example, an apparatus that "comprises," "has," "includes," or "contains" one or more elements embodies those one or more elements, but is not limited to only those elements. Likewise, a method that "comprises," "has," "includes," or "contains" one or more steps embodies those one or more steps, but is not limited to possessing only those one or more steps.

The feature or features of one embodiment may be applied to other embodiments, even though not described or illustrated, unless expressly prohibited by this disclosure or the nature of the embodiments.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

The invention claimed is:

1. A nano-scale gas chromatography (GC) module, comprising:
   an integrated sensor-GC channel module comprising:
      a first photonic crystal slab (PCS) Fano resonance filter layer comprising a hole lattice region;
      a second PCS Fano resonance filter layer; and
      a GC channel layer comprising a gas channel for separation of a plurality of analytes in a gas mixture;
   a light source; and
   a light detector, wherein:
      the hole lattice region comprises a plurality of holes arranged in a spaced periodic array to provide, based on physical parameters of the spaced periodic array, local field enhancement of light generated by the light source for increased light-matter interaction with the plurality of analytes in the gas channel; and
      in the integrated sensor-GC channel module, the GC channel layer is positioned in a tri-layer stack between the first PCS Fano resonance filter layer and the second PCS Fano resonance filter layer.

2. The nano-scale GC module according to claim 1, wherein:
   the gas channel in the GC channel layer comprises a coiled section and an extended length section; and
   in the tri-layer stack, the extended length section of the gas channel extends through a region in the GC channel layer that is stacked in proximity with the hole lattice region in the first PCS Fano resonance filter layer.

3. The nano-scale GC module according to claim 1, wherein:
   The first PCS Fano resonance filter layer comprises a first plurality of hole lattice regions;
   the second PCS Fano resonance filter layer comprises a second plurality of hole lattice regions; and
   the first plurality of hole lattice regions are substantially aligned with the second plurality of hole lattice regions in the tri-layer stack to provide a plurality of regions of local field enhancement within the tri-layer stack.

4. The nano-scale GC module according to claim 3, wherein:
the gas channel comprises a plurality of coiled sections and a plurality of extended length sections; and
each of the plurality of extended length sections of the gas channel extends through a respective one of the plurality of regions of local field enhancement within the tri-layer stack.

5. The nano-scale GC module according to claim 1, wherein:
a width of the gas channel is in a range of about 50 nanometers to about 10,000 nanometers; and
a length of the gas channel is in a range of about 1 centimeter to about 100 centimeters.

6. A nano-scale gas chromatography (GC) sensor module stack, comprising:
a first Fano resonance filter layer comprising a first hole lattice region;
a second Fano resonance filter layer comprising a second hole lattice region; and
a GC channel layer between the first Fano resonance filter layer and the second Fano resonance filter layer in a tri-layer stack, the GC channel layer comprising a gas channel for separation of a plurality of analytes in a gas mixture, wherein:
the first hole lattice region is substantially aligned with the second hole lattice region in the tri-layer stack to provide a region of local field enhancement within the tri-layer stack.

7. The nano-scale GC sensor module stack according to claim 6, wherein:
the gas channel in the GC channel layer comprises a coiled section and an extended length section; and
the extended length section of the gas channel extends through the region of local field enhancement within the tri-layer stack for increased light-matter interaction with a plurality of analytes in the gas channel.

8. The nano-scale GC sensor module stack according to claim 6, wherein a width of the gas channel is in a range of about 50 nanometers to about 10,000 nanometers.

9. The nano-scale GC sensor module stack according to claim 6, wherein a length of the gas channel is in a range of about 1 centimeter to about 100 centimeters.

10. The nano-scale GC sensor module stack according to claim 6, wherein:
the first hole lattice region comprises a plurality of first hole lattice regions;
the second hole lattice region comprises a plurality of second hole lattice regions; and
the first plurality of hole lattice regions are substantially aligned with the second plurality of hole lattice regions in the tri-layer stack to provide a plurality of regions of local field enhancement within the tri-layer stack.

11. The nano-scale GC sensor module stack according to claim 10, wherein:
the gas channel in the GC channel layer comprises a plurality of coiled sections and a plurality of extended length sections; and
each of the plurality of extended length sections of the gas channel extends through a respective one of the plurality of regions of local field enhancement within the tri-layer stack for increased light-matter interaction with a plurality of analytes in the gas channel at a plurality of different locations along the gas channel.

12. A gas chromatography (GC) module, comprising:
a light source to provide light;
an integrated sensor-GC channel stack comprising:
a GC fluidic layer;
a first Fano resonance filter layer; and
a second Fano resonance filter layer, wherein the GC fluidic layer is positioned in a tri-layer stack between the first Fano resonance filter layer and the second Fano resonance filter layer, at least one of the first Fano resonance filter layer and the second Fano resonance filter layer comprising a hole lattice region arranged to provide a region of local field enhancement of the light in the GC fluidic layer; and
a light detector array to sense light-matter interaction between the light and a plurality of analytes in the GC fluidic layer.

13. The GC module according to claim 12, wherein the GC fluidic layer comprises a gas cavity.

14. The GC module according to claim 12, wherein:
the first Fano resonance filter layer comprises a silicon nanomembrane (NM) photonic crystal slab (PCS) Fano resonance filter layer; and
the second Fano resonance filter layer comprises a silicon NM PCS Fano resonance filter layer.

15. The GC module according to claim 12, wherein the GC fluidic layer comprises a gas channel coated with a polymer, the gas channel comprising a coiled section and an extended length section.

16. The GC module according to claim 15, wherein the extended length section of the gas channel extends through a region in the GC fluidic layer that is stacked in proximity with the hole lattice region.

17. The GC module according to claim 15, wherein a width of the gas channel is in a range of about 50 nanometers to about 10,000 nanometers, and a length of the gas channel is in a range of about 1 centimeter to about 100 centimeters.

18. The GC module according to claim 12, wherein:
the first Fano resonance filter layer comprises a first hole lattice region;
the second Fano resonance filter layer comprises a second hole lattice region; and
the first hole lattice region is substantially aligned with the second hole lattice region in the tri-layer stack to provide a region of local field enhancement within the tri-layer stack.

19. The GC module according to claim 12, wherein:
the first Fano resonance filter layer comprises a first plurality of hole lattice regions;
the second Fano resonance filter layer comprises a second plurality of hole lattice regions; and
the first plurality of hole lattice regions are substantially aligned with the second plurality of hole lattice regions in the tri-layer stack to provide a plurality of regions of local field enhancement within the tri-layer stack.

* * * * *